US007442393B2

(12) United States Patent
Rathod et al.

(10) Patent No.: US 7,442,393 B2
(45) Date of Patent: Oct. 28, 2008

(54) HERBAL EXTRACTS OF SALICORNIA SPECIES, PROCESS OF PREPARATION THEREOF, USE THEREOF AGAINST TUBERCULOSIS

(75) Inventors: Meena Rajnika Rathod, Gujarat (IN); Bhupendra D. Shethia, Gujarat (IN); Jayant B. Pandya, Gujarat (IN); Pushpito K. Ghosh, Gujarat (IN); Prakash J. Dodia, Gujarat (IN); Brahm S. Srivastava, Uttar Pradesh (IN); Ranjana Srivastava, Uttar Pradesh (IN); Anil Srivastava, Uttar Pradesh (IN); Vinita Chaturvedi, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/819,220

(22) Filed: Jun. 26, 2007

(65) Prior Publication Data

US 2007/0248704 A1    Oct. 25, 2007

Related U.S. Application Data

(60) Division of application No. 11/045,490, filed on Jan. 31, 2005, which is a continuation of application No. 10/829,400, filed on Apr. 22, 2004, now abandoned, which is a continuation of application No. 10/651,212, filed on Aug. 29, 2003, now abandoned.

(51) Int. Cl.
*A01N 65/00* (2006.01)
*A61K 36/00* (2006.01)
(52) U.S. Cl. .................................. 424/725; 514/924
(58) Field of Classification Search ............. 424/725; 514/924
See application file for complete search history.

(56) References Cited

FOREIGN PATENT DOCUMENTS

| DE | 19630323 C1 | 8/1997 |
|---|---|---|
| FR | 2657011 A1 | 7/1991 |
| WO | WO 03/079817 A | 10/2003 |

OTHER PUBLICATIONS

Snell NJ. "The treatment of tuberculosis: current status and future prospects." Expert Opin Investig Drugs, vol. 7, No. 4 (Apr. 1998) 545-552.*
Anwar et al. "Analytical characterization of salicornia bigelovii seed oil cultivated in Pakistan" J. Agr. Food Chem. 50:4210-4214 (2002).
Bhosale et al. "Antifungal activity of some marine organisms from India, against food spoilage Aspergillus strains" Mycopathol. 147:133-138 (1999).
Bhosale et al. "Antifouling potential of some marine organisms from India against species of bacillus and pseudomonas Mar." XP-002278324 Biotechnol. 4:111-118 (2002).
Dave et al. "Effect of herbal antifungal agents on 33 trichophyton isolates" Proc. Nat. Acad. Sci. India 71:149-155 (2001).
Faulds et al. "A major component of cell walls, ferulic acid, influences feruloyl esterase production in aspergillus niger" Biochem. Soc. Trans. 24:386s (1996).
http://web.archive.org/web/*/http://www.public.iastate.edu/~bot.512/lectures/development&hormones_512.pdf.
http://en.wikipedia.org/wiki/chloroform.
http://www.m-w.com./cgi-bin/dictionary?book=dictionary&va+bioactive.
http://www.ibiblio.org/pfaf/cgi-bin/arr_html?salicornia+europaea.
http://people.westminstercollege.edu/faculty/tharrison/gslplaya99/pickleweed.htm.
http://www.naturalfoodsmerchandiser.com/AsP/802/display-article.
Khan et al. "Effect of salinity on the growth and ion content of salicornia rubra" Commun. Soil Sci. Plant Anal. 32:2965-2977 (2001).
Lin et al. "Liquid Chromatographic-electrospray mass spectrometric study of the Phthalides of Angelica sinesis and chemical changes of Z-ligustilide" J. Chromat. A 810:71-79 (1998).
Pennings et al. "Feeding preferences of a generalist salt marsh carb: Relative importance of multiple plant traits" Ecol. 79:1968-1979 (1998).
Renard et al. "Cell wall phenolics and plysaccharides in different tissues of quinoa chenopodium quinoa willd" J. Sci. Food Agric. 79:2029-2034 (1999).
Schwartzkopf et al. "Potassium, calcium and magnesium—How they relate to plant growth" USGA Green Section Record pp. 1-2 (1972).
Siska et al. "Latitudinal variation in palatability of Salt-Marsh Plants: Which traits are responsible?" Ecol. 83:3369-3381 (2002).
Thangam et al. "Larvicidal activity of mangrove plant extracts and synergistic activity of rhizophora apiculata with pyrethrym against culex quinquefasciatus" Int. J. Pharmacog. 35:69-71 (1997).
The ORNL recycler, Susan R. Michaud, Producer: Lockheed Martin: Oak Ridge National Laboratory (1996).
International Search Report for PCT/IN03/00292 dated May 13, 2004.

\* cited by examiner

*Primary Examiner*—Amy L Clark
(74) *Attorney, Agent, or Firm*—Nixon & Vanderhye P.C.

(57) ABSTRACT

The present invention relates to extracts of *Salicornia* species. The present invention particularly relates to extracts of *Salicornia* species which show antitubercular activity. The present invention also relates to a process for the preparation of novel extracts of *Salicornia* species with antitubercular activity and also to the use thereof for the treatment of tuberculosis.

20 Claims, 3 Drawing Sheets

HERBAL EXTRACTS OF SALICORNIA SPECIES, PROCESS OF PREPARATION THEREOF, USE THEREOF AGAINST TUBERCULOSIS

CROSS-REFERENCE TO RELATED APPLICATIONS

This application is a division of application Ser. No. 11/045,490, filed Jan. 31, 2005, pending; which is a continuation of application Ser. No. 10/829,400, filed Apr. 22, 2004, abandoned; which is a continuation of application Ser. No. 10/651,212, filed Aug. 29, 2003, abandoned; the entire contents of which are hereby incorporated by reference in this application.

FIELD OF THE INVENTION

The present invention relates to novel extracts of *Salicornia* species. The present invention particularly relates to novel extracts of *Salicornia* species which show antitubercular activity. The present invention also relates to a process for the preparation of novel extracts of *Salicornia* species with antitubercular activity and also to its use for treatment of tuberculosis.

BACKGROUND OF THE INVENTION

Antitubercular chemotherapeutic drugs presently used all over the world comprise primarily of synthetic drugs, e.g., isoniazid (i.e., isonicotinic acid hydrazide), used singly or in combination with sodium PAS (sodium para amino salicylate), ISONEX (isoniazid), ERBAZIDE (calcium methanesulfonate of isoniazid), cyclocerine, morphazinamide hydrochloride, rifampicin, MYAMBUTOL (ethambutol), sparfloxicin, etc. which were developed subsequent to the synthesis of the antibiotic streptomycin.

While there are cures for tuberculosis by using the above mentioned drugs along with the BCG vaccination, several drawbacks are noticed, especially in terms of side effects of such drugs, the requirement of prolonged intake/duration of therapy. Another problem observed is that even after treatment, some mycobacterium continue to reside in the subject. It is therefore imperative to create alternatives to the above class of drugs so that either the dosage or the intake duration is reduced or the problem of resistance to the drugs is obviated.

Reference is made to K. Usha et al., who in a paper entitled "Antitubercular potential of selected plant materials" in *Journal of Medicinal and Aromatic Plant Sciences*, 22/4A-23/1A, 182-184 (Eng.) (2000-2001), describe the antitubercular potential of the plants viz., neem, tulsi, garlic, ginger and adhatoda, which were tested by in vitro culture using 100 mL of aqueous puree (50% w/v) of plant material added to sputum and then inoculated in to LJ medium. All the plant extracts arrested the growth of *Mycobacterium tuberculosis*, which was ascribed to enzymic and nonenzymic antioxidants such as catalase, peroxidase, total carotene, ascorbic acid, tocopherol, and polyphenols thus preventing tissue damage by ROS (reactive oxygen species). Besides the large quantity of potion that needs to be applied, it is unclear as to the extent of inhibition and the MIC of the potion.

Reference is made to N. Lall et al. in a paper entitled "In vitro inhibition of drug-resistant and drug-sensitive strains of *Mycobacterium tuberculosis* by ethnobotanically selected South African plants" in *Journal of Ethnopharmacology*, 66, 347-354 (1999), which describes the preliminary screening of 20 South African medicinal plant extracts against a drug-sensitive strain, H37Rv, of *Mycobacterium tuberculosis* by agar plate method (Middlebrook and Cohn, 1958). Herein the author ascribes 14 out of 20 acetone extracts showing inhibitory activity at concentration of 500 µg/ml whereas acetone as well water extracts of plant species namely *Cryptocarya latifolia, Euclea natalensis, Helichrysum melanacme, Nidorella anomala* and *Thymus vulgaris* indicated MIC of 100 µg/ml against H37Rv strain by radiometric method.

Reference is also made to C. L. Cantrell et al. in a review article entitled "Antimycobacterial plant terpenoids" in *Journal of Planta Medica*, 67(8), 685-694 (Eng.) (2001), which covers recent report on plant-derived terpenoids that have demonstrated moderate to high activity in in vitro bioassays against *M. tuberculosis*. In this review, mono-, sesqui-, di- and triterpenes & sterols, their structural analogue and semi synthetic derivatives have been discussed with particular emphasis on the structural features essential for antimycobacterial activity.

Reference is made to Ma, Junrui in a patent entitled "Compositions containing herbal medicine for pulmonary tuberculosis" No. CN 1265315 A 6 Sep. 2000, 4 pp. (Chinese) (2001), which contains the different forms of composition (aerosol, inhalant, tablet, capsule, powder, oral concentrate and liquid) for treating pulmonary tuberculosis composed of *Taraktogenos, Coptis, Stemona, Cordyceps, Scutellaria, Lonicera japonica, Forsythia vahl, Herba violae, Anemarrhena, Salvia miltiorrhiza, Fructus mume, Ginkgo biloba, Anacamptis pyoamidalis Richard, Polygonatum, Glycyrrhiza, Polygonum multiflorum thunb, Brunella vulgaris, Cirsium japonicum*, leaf of *Thuja orientalis, Sguisorba officinalis, Heracleum*, common *Andrographis, Houttuynia, herba artemisiae* and *Magnolia officinalis*. However the drawback here is the use of multiple herbs for the purpose of elucidating the positive gains of plant against *mycobacterium tuberculosis* and without referring to MIC level either of individual herb or collectively of the combination.

Reference is made to a paper titled "Preliminary antimicrobial screening four South African *Asteraceae* species" by F. Salie et al. in *Journal of Ethanopharmacology*, 52, 27-33 (1996) wherein the author has investigated the flora of the Western Cape—a part of Cape Floral kingdom in South Africa. The author ascribes the efficacy of four *Asteraceae* species (*Arctopis auriculanta, Eriocephalus africanus L., Felicia erigeroides DC.* and *Helichrysum crispum (L.) D. Don.*) exhibiting selective anti-microbial activity to various degree for *Mycobacterium smegmatis*. Identifying the 8500 µg/ml of MIC in leaves of *Arctopis auriculanta*. The drawback of the invention is the very high MIC value. Reference is also made to Internet website benefits@coqui.net on *Salicornia* plant, where use of *Salicornia* plant as a source of edible oil and use of dried crushed stems as fuel briquettes or particleboard are reported. However, there is no mention of bioactivity of the plant.

Reference is also made to U.S. patent application Ser. No. 10/106,334 dt. 26th Mar. 2002 by P. K. Ghosh et al. wherein a vegetable salt preparation from residual dry matter after removal of seeds using halophyte has been described to maximize value derived from the plant. However this application does not provide any use of the plant for drug/medicinal purpose.

Reference is made to *Wealth of India*, vol. IX RH-SO which documents various bioresources of India and application thereof has listed *Salicornia* Linn. and its taxonomy beside use of the species as fodder. The plant is also listed in

*Flora of India* by Hooker (1889), However no mention is made in both documents on any kind of bioactivity associated with *Salicornia*.

OBJECTS OF THE INVENTION

The main object of the present invention is to provide an antitubercular extract from marshy succulent halophytic plants such as those of the *Salicornia* species available naturally in the coastal regions of India and elsewhere, and to a process for the preparation of such antitubercular extract.

Another object is to produce an active extract from a single plant, and more preferably a single plant part.

It is another object of the invention to provide an active extract from a non-traditional source which also obviates the drawbacks of prolonged duration of therapy due to its high activity.

It is another object of the invention to provide an active antitubercular extract from *Salicornia* species which has a high shelf life without significant loss of activity.

It is another object of the invention to provide a process for the preparation of novel antitubercular extracts from *Salicornia* species which is simple and economical.

It is another object of the invention to provide an antitubercular extract of *Salicornia* species which enables overcoming the problem of drug resistance in subjects treated with synthetic drugs.

SUMMARY OF THE INVENTION

Accordingly, the present invention provides a novel bioactive fraction from extracts of *Salicornia* species with antitubercular activity.

In one embodiment of the invention, the *Salicornia* species comprises of *Salicornia brachiata*.

In another embodiment of the invention, the *Salicornia brachiata* is a fully matured plant.

In another embodiment of the invention, the extract comprises extracts from parts of *Salicornia* plant selected from the group consisting of whole plant without root, roots, spikes, husk and seeds.

In another embodiment of the invention, the extract comprises an aqueous plant extract with 100% water.

In another embodiment of the invention, the extract comprises an alcohol extract.

In a further embodiment of the invention, the alcohol comprises methanol or butanol.

In a further embodiment of the invention, the bioactive fraction is obtained from an extract of *Salicornia brachiata* in methanol:water in a range of 95:5 to 1:1.

In another embodiment of the invention, the bioactive fraction is obtained from an extract in methanol:chloroform of 1:1.

In another embodiment of the invention, the plant part is the root.

In another embodiment of the invention, the bioactive fraction from crude extract is selected from the group consisting of neat butanol extract, methanol:chloroform (1:1) extract, neat methanol extract, methanol:water (1:1) extract, pure water extract.

In another embodiment of the invention, the yields of the bioactive fraction comprises 10%, 13%, 51%, 10% and 9% respectively.

The present invention also relates to a process for the preparation of a bioactive fraction from extracts of halophytic plant of *Salicornia* species useful as anti tubercular agent which comprises (a) collection of the halophytic plant at fully maturity stage
(b) washing the plant with tap water followed by deionised water
(c) removing extraneous matter, separation and processing of the plant to obtain plant parts
(d) drying, chopping and pulverizing the plant parts to a mesh size ranging from 16-20
(e) soaking the dried, chopped and pulverized plant parts in a solvent and extracting all soluble matter to obtain an extract,
(f) concentrating the extract
(g) freeze drying the concentrated extract to get a solid residue
(h) fractionating the solid residue to obtain a bioactive fraction.

In one embodiment of the invention, the *Salicornia* species comprises of *Salicornia brachiata*.

In another embodiment of the invention, the *Salicornia brachiata* is a fully matured plant.

In another embodiment of the invention, the extract comprises extracts from parts of *Salicornia* plant selected from the group consisting of whole plant without root, roots, spikes, husk and seeds.

In another embodiment of the invention, the solvent is selected from the group consisting of 100% water, alcohol and alcohol-water mixtures.

In a further embodiment of the invention, the alcohol comprises methanol or butanol.

In a further embodiment of the invention, the solvent comprises 100% water.

In a further embodiment of the invention, the alcohol-water mixture comprises methanol: Water in a range of 95:5 to 1:1.

In another embodiment of the invention, the bioactive fraction from extract is selected from the group consisting of neat butanol extract, methanol:chloroform (1:1) extract, neat methanol extract, methanol:water (1:1) extract, pure water extract.

In another embodiment of the invention, the yields of the bioactive fraction comprises 10%, 13%, 51%, 10% and 9% respectively.

In another embodiment of the invention, the bioactive fraction is obtained from the extract using methanol:chloroform in a ratio of 1:1.

In another embodiment of the invention, the bioactive fraction is obtained from the extract using butanol.

In another embodiment of the invention, the bioactive fraction is obtained from the extract using chloroform.

In another embodiment of the invention, the bioactive fraction is obtained from the extract using methanol.

In another embodiment of the invention, the bioactive fraction is obtained from the extract using water.

In another embodiment of the invention, the plant part is the root.

In another embodiment of the invention, the water fraction is obtained at a temperature in the range of 80-90° C.

In another embodiment of the invention, the fractionation is carried out at ambient temperature.

In another embodiment of the present invention, the plant material is washed and dried at a temperature of 20 to 35° C. till the moisture content is in the range of 0.5 to 1.5%.

In another embodiment of the present invention the pulverized material is soaked in deionised water and heated on water bath in the temperature range 80 to 90° C. for a period of 72-120 hours.

In still another embodiment of the present invention, the extract solution is concentrated by known techniques in a temperature range of 45 to 55° C. or at ambient temperature through aqueous herbal concentrator.

In still another embodiment of the present invention, the concentrated extract may be freeze dried in the temperature range of −50 to −60° C. for a period of 8 to 16 hours.

In still another embodiment of the present invention, the extract is fractionated in solvent mixtures having different polarity.

The present invention also relates to the use of a bioactive fraction obtained from an extract of *Salicornia* species as an antitubercular agent.

In one embodiment of the invention, the *Salicornia* species comprises of *Salicornia brachiata*, preferably a fully matured plant.

In another embodiment of the invention, the extract comprises extracts from parts of *Salicornia* plant selected from the group consisting of whole plant without root, roots, spikes, husk and seeds.

In another embodiment of the invention, the extract comprises an aqueous plant extract with 100% water.

In another embodiment of the invention, the extract comprises an alcohol extract.

In a further embodiment of the invention, the alcohol comprises methanol or butanol.

In a further embodiment of the invention, the bioactive fraction is obtained from an extract of *Salicornia brachiata* in methanol:water in a range of 95:5 to 1:1.

In another embodiment of the invention, the bioactive fraction is obtained from an extract in methanol:chloroform of 1:1.

In another embodiment of the invention, the plant part is the root.

In another embodiment of the invention, the bioactive fraction from crude extract is selected from the group consisting of neat butanol extract, methanol:chloroform (1:1) extract, neat methanol extract, methanol:water (1:1) extract, pure water extract.

In another embodiment of the invention, the yields of the bioactive fraction comprises 10%, 13%, 51%, 10% and 9% respectively.

In another embodiment of the invention, the bioactive fraction is used in an amount of 6.25 to 80 µg/ml.

The present invention also relates to a method for the treatment of tuberculosis comprising administering to a subject suffering therefrom, a pharmaceutically effective amount of an antitubercular fraction obtained from *Salicornia* species.

In one embodiment of the invention, the method comprises administering either bioactive fraction or the crude extract of *Salicornia* species to the subject.

In another embodiment of the invention, the *Salicornia* species comprises of *Salicornia brachiata*.

In another embodiment of the invention, the *Salicornia brachiata* is a fully matured plant.

In another embodiment of the invention, the extract comprises extracts from parts of *Salicornia* plant selected from the group consisting of whole plant without root, roots, spikes, husk and seeds.

In another embodiment of the invention, the extract comprises an aqueous plant extract with 100% water.

In another embodiment of the invention, the extract comprises an alcohol extract.

In a further embodiment of the invention, the alcohol comprises methanol or butanol.

In a further embodiment of the invention, the bioactive fraction is obtained from an extract of *Salicornia brachiata* in methanol:water in a range of 95:5 to 1:1.

In another embodiment of the invention, the bioactive fraction is obtained from an extract in methanol:chloroform of 1:1.

In another embodiment of the invention, the plant part is the root.

In another embodiment of the invention, the bioactive fraction from crude extract is selected from the group consisting of neat butanol extract, methanol:chloroform (1:1) extract, neat methanol extract, methanol:water (1:1) extract, pure water extract.

In another embodiment of the invention, the yields of the bioactive fraction comprises 10%, 13%, 51%, 10% and 9% respectively.

In another embodiment of the invention, the bioactive fraction is used in an amount of 20 to 80 µg/ml.

In another embodiment of the invention, the crude aqueous extract of *Salicornia brachiata* root part shows MIC of 50 µg/ml against *Mycobacterium tuberculosis*, H37Rv.

In another embodiment of the invention, one or more fractions of *Salicornia* species are administered to the subject and show activity against *Mycobacterium tuberculosis* H37Rv and show MIC of 25 µg/ml.

In another embodiment of the invention, the butanol fraction, methanol:chloroform (1:1) fraction and the methanol fraction show up to 75% inhibition in growth of *Mycobacterium tuberculosis* H37Rv at a dose of 6.25 µg/ml.

DETAILED DESCRIPTION OF THE INVENTION

Figure 1:
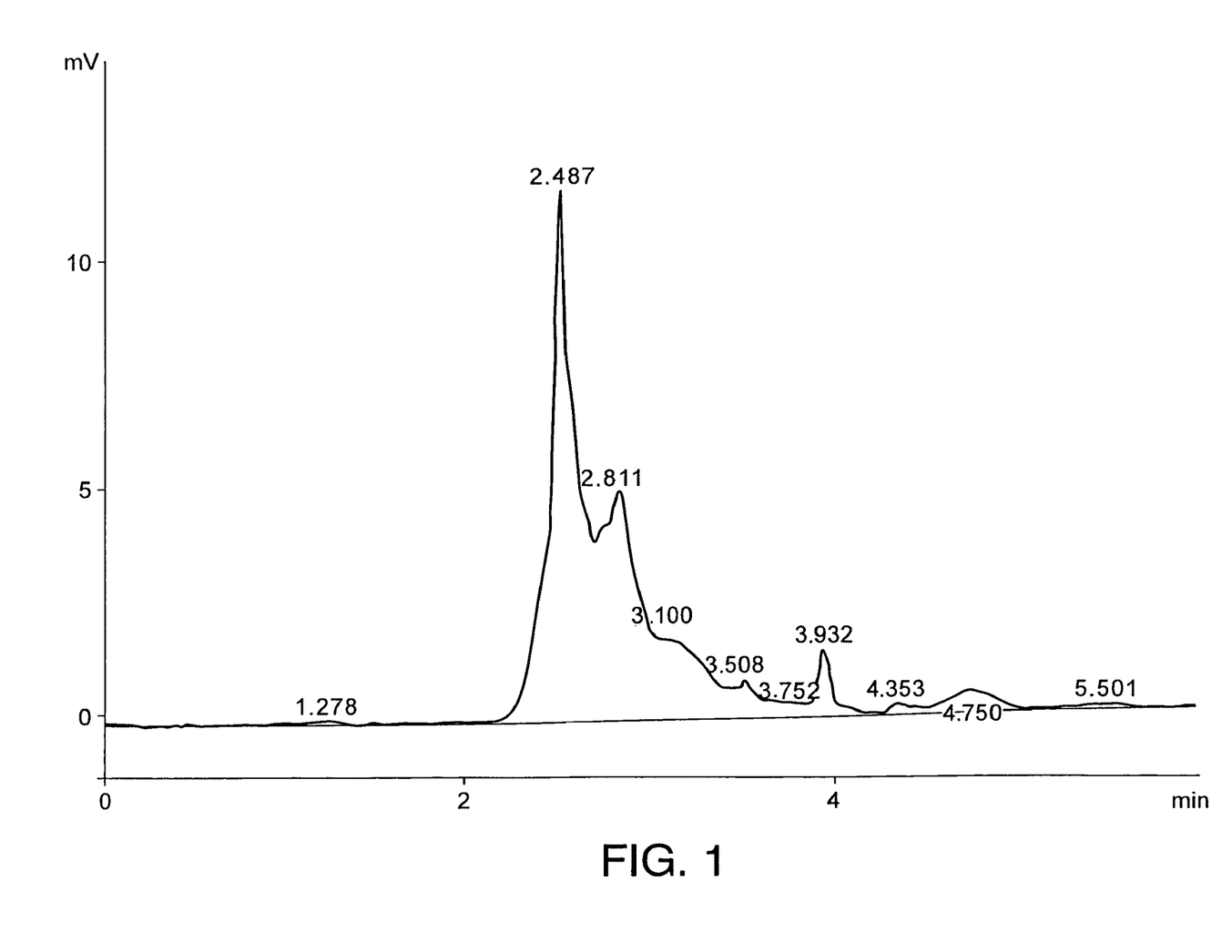
FIG. 1 is a HPLC profile of the second fraction F2 at 220 nm, taken on an analytical HPLC instrument using RP-18 reverse phase column and 1:1 acetonitrile/methanol isocratic eluting solvent at a flow rate of 1 mL/minute.
Figure 2:
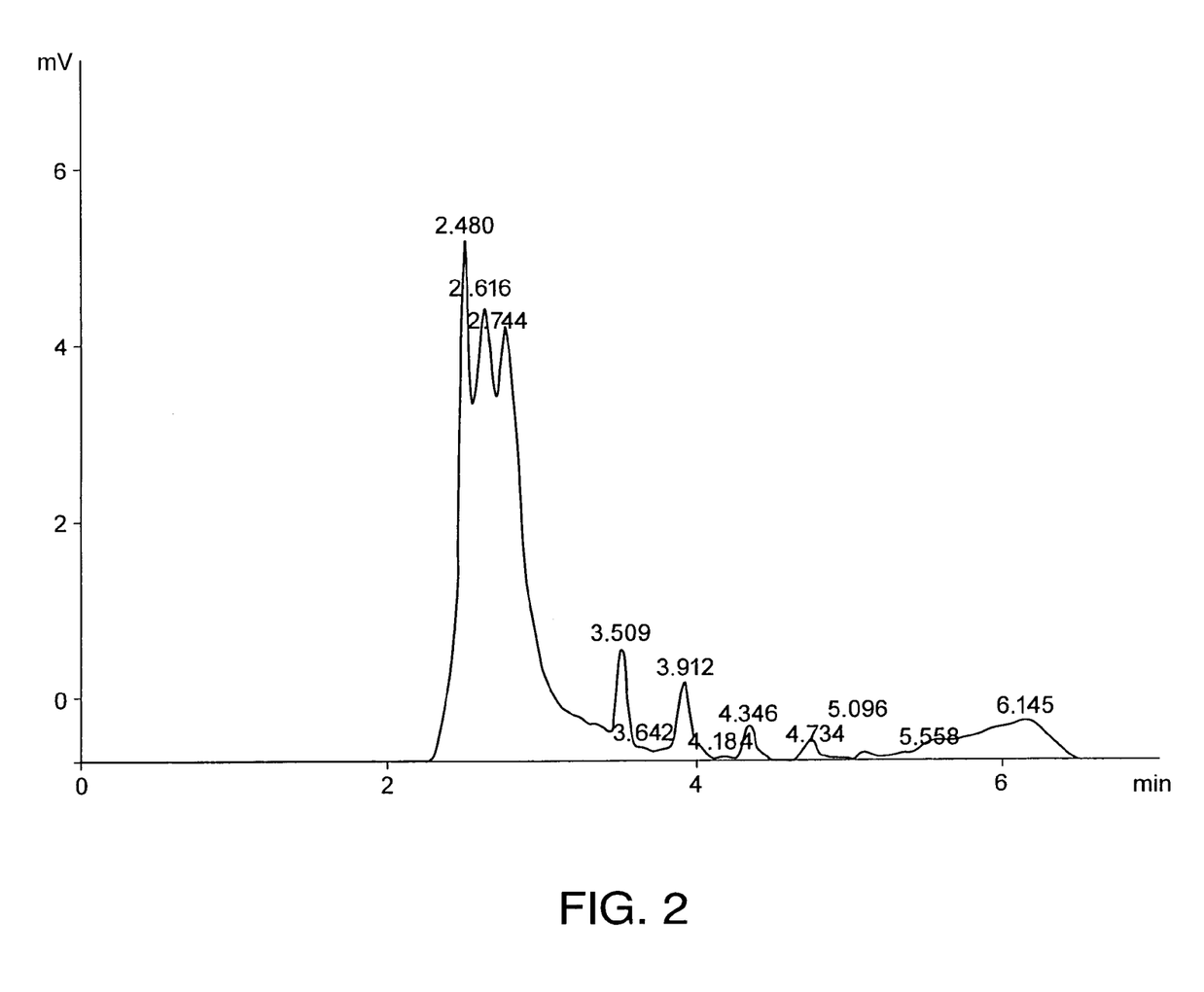
FIG. 2 is a HPLC profile of the third fraction F3 at 220 nm, taken on an analytical HPLC instrument using RP-18 reverse phase column and 1:1 acetonitrile/methanol isocratic eluting solvent at a flow rate of 1 mL/minute.
Figure 3:
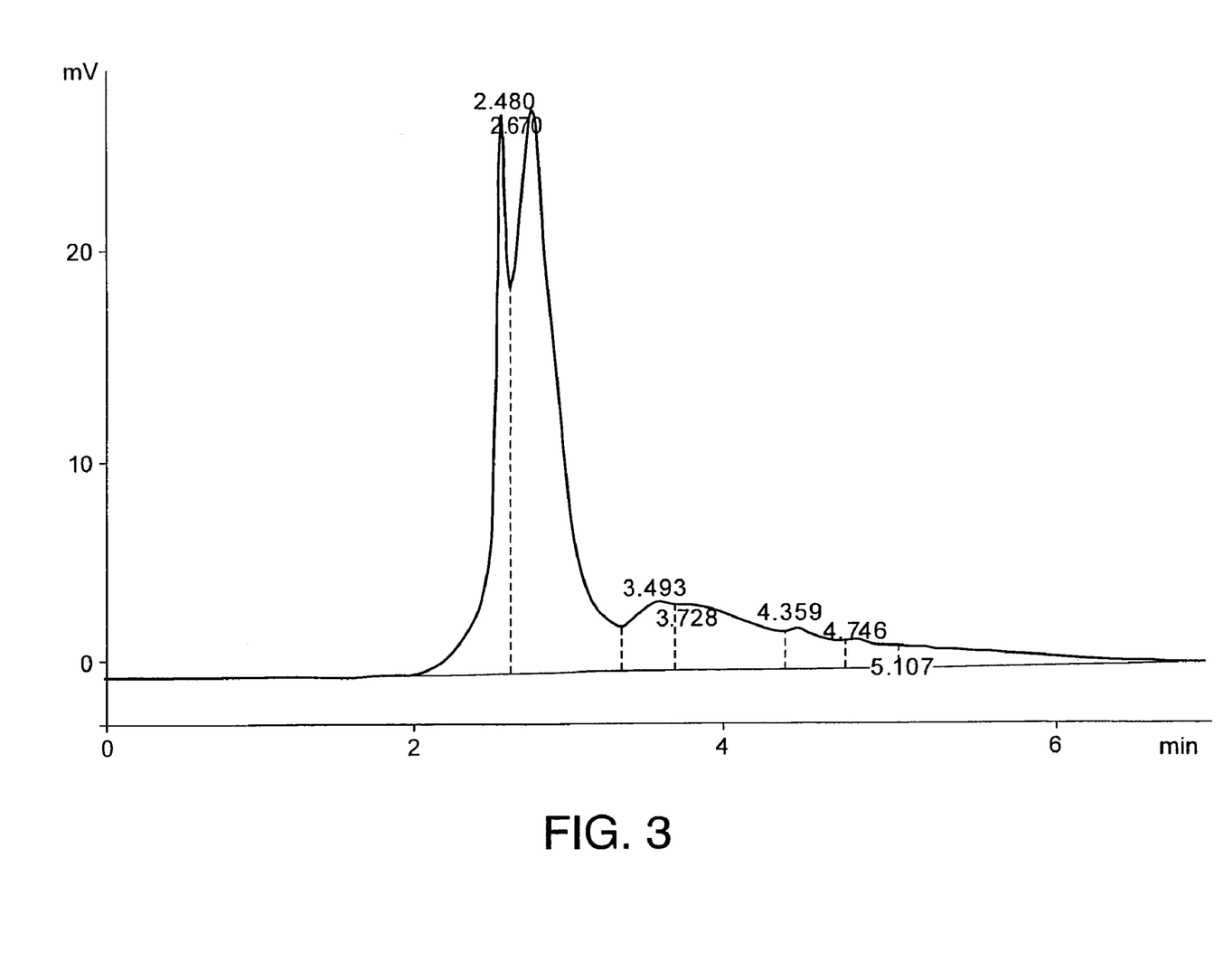
FIG. 3 is a HPLC profile of the fourth fraction F4 at 220 nm, taken on an analytical HPLC instrument using RP-18 reverse phase column and 1:1 acetonitrile/methanol isocratic eluting solvent at a flow rate of 1 mL/minute.

The present invention relates to the analysis and study of *Salicornia* species in order to obtain bioactive fractions or crude extracts thereof which may possess antitubercular activity. *Salicornia* species such as *Salicornia brachiata* is available in the marshy lands of Western India and is a halophytic plant. *Salicornia brachiata* plant belonging to chenopodiaceae family was identified and collected at fully matured stage. The *Salicornia* species is growing in salt marshes of Asia/Africa, Europe and North America.

The present invention therefore provides novel bioactive fractions from and crude extracts of *Salicornia* species. The present invention also relates to a process for the preparation of a plant extract of *Salicornia* species with antitubercular activity which comprises collection of plant at full maturity, washing the plant with using tap water followed by deionised water, removal of all extraneous matter, separation and processing of the plant material to get the desired part, drying, chopping & pulverizing to a certain mesh size, soaking in the solvent & extracting all the soluble matter, concentrating the extract by conventional technique, freeze drying the concentrated extract to get solid residue, fractionating the extract into five fractions using butanol, chloroform, methanol and water, either singly or in combination, testing the crude extract and fractions in vitro and in vivo for antitubercular activities, specifically against *Mycobacterium tuberculosis* H37Rv, and recording HPLC profiles for the fractions to serve as finger print.

The plant material is preferably washed and dried at a temperature range of 20 to 35° C. until the moisture content is in the range of 0.5 to 1.5 percent. The plant material prior to soaking is preferably pulverized and the sieved material in the range of 16-20 mesh size sieve may be selected for further treatment. The extracts and fractions were both tested in vitro and in vivo for antitubercular activities.

The plant taxon is an annual/perennial, small erect, branched herb, 30-40 cms. in height. It has succulent and articulated stem, opposite branches and short stem internodes. The leaves are reduced to scales, forming a short sheath with rudimentary lamina and sharply pointed tips.

Flowers are trinate, embedded in cavities along with the upper part of the branches. Seed spikes consist of cymes containing three flowers. The middle flower in cymes is noticeably higher than two lateral ones, resulting in at triangular conformation. Stamen one or two, style distinct, stigma subulate, embryo hook both ends pointing downwards. Seeds are erect, compressed, membranous and exalbuminous.

The method of the invention comprises:

1. Collecting *Salicornia brachiata* plant material at fully matured stage.
2. Washing and drying the plant material at ambient temperature in the range of 25 to 37° C. while maintaining the moisture in the range of 0.5-1.5%.
3. Reducing the size of the plant material by pulverizing and selecting the material in the size range of 16-20 mesh sieve.
4. Soaking the plant material in deionized water and heated up to 80-90° C. temperature, and repeating the soaking step five times with fresh deionized water at an interval of 24 hours.
5. Concentrating the extract by conventional/herbal concentrator techniques.
6. Freeze drying the concentrated extract in the temperature range of −50 to −60° C. for a period in the range of 8 to 16 hours so as to recover 18-20% yield of crude.
7. Fractionating the extract into five fractions F1 (5-15% yield) in butanol, F2 (13-30% yield), in 50% methanol-chloroform F3 (34-51% yield), in methanol F4 (9-15% yield) in 50% methanol-water and F5 (3-9% yield) in Water.
8. Also their respective compounds present in the chromatogram developed at wavelength ranging from 220 to 254 nm, producing various peaks under varied eluant system.
9. Bioassay and testing the extract and fractions in vitro and in vivo for antitubercular activities.
10. Subfractionating of one of the above active fraction and testing all the three sub fractions in vitro for antitubercular activity.
11. Also their respective compounds present in chromatogram developed at 220 nm, producing peak under varied eluent system.

According to the present invention, the plant was identified and necessary material was collected from the field at fully matured stage. This material was thoroughly washed with deionized water to remove mud, dust particles and foreign matter. The cleaned plant material was dried at room temperature under shade for a period of 3 to 4 weeks. The plant material was pulverized and sieved to obtain 16 to 20-mesh size powder, soaked in deionised water and heated on water bath at 80-90° C. for 5-6 hours. The extraction cycle was repeated for five times using fresh deionised water and filtered under vacuum in Buckner funnel. All the filtrates were then mixed and concentrated using known technique to obtain crude extract. This concentrated extract was freeze dried to obtain moisture-free crude extract in the powder form. This extract was initially tested in vitro and after several repeated positive tests the extract was further tested for in vivo antitubercular activity. The extract was fractionated with solvent mixtures of different polarity and each fraction was tested in vitro and in vivo antitubercular activity. One of the active fraction was also sub fractionated and tested in vitro.

EXAMPLE 1

The halophytic plant material was collected from coastal area of Gujarat near Bhavnagar district, located at 21° 75' N Latitude & 72° 17' E Longitude to 21° 09' N latitude and 72° 00' E longitude at a varying altitude of 10-27' above the mean sea level of the Gulf of Cambay. The plant material was collected from the above site during its maturity stage in February-March. It was washed off all the debris/mud with tap water followed with deionized water. It was further processed and separated into various parts, i.e., whole plant without root, root, spikes, husk and seeds. These parts were air dried at ambient temperature. The dried plant material was powdered in mini grinding mill to obtain fine powder of the mesh size of 16 to 20μ. The parts were then further processed for crude extract preparation with the solvents: methanol-water (95:5), methanol-water (1:1) at ambient temperature and pure water at 80-90° C. These crude extracts were subjected to bioassay for antitubercular activity. The results of bioactivity for many parts found are as under:

TABLE 1

| Sr | Plant part | Solvent System | % Mice surviving on Different days |
|---|---|---|---|
| 1 | Root | Methanol-Water (1:1) | 17% up to 28 days |
| 2 | Root | Water (100%) | 17% up to 35 days |
| 3 | Whole Plant without root | Water (100%) | 17% up to 24 days |
| 4 | Seed husk | Methanol-Water (95:5) | 17% up to 23 days |

EXAMPLE 2

The most active extract from the example of Example 1, i.e., the water extract of root which yielded 18-20% on basis of dry material, was fractionated into 5 fractions. The first fraction (F1) was obtained through extraction with neat butanol, the residue was subjected to extraction with methanol-chloroform (1:1) to yield the second fraction (F2), the residue was then subjected to extraction with neat methanol to yield the third fraction (F3), the residue was then subjected to extraction with methanol-water (1:1) to yield the fourth fraction (F4) and the residue was then treated with pure water to obtain the fifth fraction (F5) after filtration. The yields of F1, F2, F3, F4 and F5 were 10%, 13%, 51%, 10%, and 9%, respectively. All the five fractions showed MIC of 25 μg/ml, whereas F2, F3 and F4 show 75% inhibition even at the concentration of 6.25 μg/ml as compared to control. The HPLC profiles of F2, F3 and F4 at 220 nm, taken on an analytical HPLC instrument using RP-18 reverse phase column and 1:1 acetonitrile/methanol isocratic eluting solvent at a flow rate of 1 mL/minute, are shown in FIGS. 1, 2 and 3 respectively. Details are given in Tables 2, 3 and 4 respectively below at the end of the examples.

EXAMPLE 3

*Salicornia brachiata* was again collected after one year from the same location defined in Example 1. Collection was made at the same growth stage and the process of preparation of crude extract was repeated with the root of the plant as in Example 1. The extract was subjected to an identical bioassay as described in Example 1. The extract inhibited growth to *M. tuberculosis* H37RV in vitro at 50 µg/ml while in vivo tests showed 10-fold less load of bacilli in the lungs of mice receiving treatment.

The *Salicornia* plant having active components was collected at fully matured stage and used for the extract preparation. The plant material is washed with tap water followed by deionized water to remove mud, dust particles and other foreign matter, dried, cut to small pieces, pulverized and soaked in the deionized water. The soaked plant material is heated on water bath at 80-90° C. temp. The water-soluble extract was decanted and filtered. The above process was carried out for three to five days so as to recover all the water-soluble material. The filtrate was concentrated through known technique/new techniques of herbal concentrator and subsequently dried on Freeze Drier to obtain solid active extract in powder form. The active extract was fractionated in to five fractions using butanol, chloroform, methanol and water. The present process is simple, rapid, and has high and efficient recovery, thus yielding a highly active extract containing all the vital ingredients, which are effective for curing the tuberculosis disease.

Specifically, the invention relates to the preparation of herbal extracts of *Salicornia brachiata,* an edible salt tolerant oil bearing plant, in a manner that leads to maximum bioactivity of extract against *Mycobacterium tuberculosis* and simultaneously allows maximum utilization of the plant.

TABLE 2

For FIG. 1

| No. | Time | Area | Height | MK | Concentration |
|---|---|---|---|---|---|
| 1 | 1.278 | 1308 | 93 | | 0.5006 |
| 2 | 2.487 | 121678 | 11769 | | 46.5607 |
| 3 | 2.811 | 75098 | 5073 | V | 28.7365 |
| 4 | 3.100 | 28267 | 1760 | V | 10.8165 |
| 5 | 3.508 | 9853 | 805 | V | 3.7703 |
| 6 | 3.752 | 2501 | 351 | V | 0.9571 |
| 7 | 3.932 | 9700 | 1491 | V | 3.7116 |
| 8 | 4.353 | 1739 | 249 | V | 0.6652 |
| 9 | 4.750 | 9066 | 491 | V | 3.4693 |
| 10 | 5.501 | 2123 | 101 | V | 0.8123 |
| | | 261332 | 22184 | | 100.0000 |

TABLE 3

For FIG. 2

| No. | Time | Area | Height | MK | Concentration |
|---|---|---|---|---|---|
| 1 | 2.480 | 36650 | 6030 | | 16.9907 |
| 2 | 2.616 | 42758 | 5267 | V | 19.8224 |
| 3 | 2.744 | 75979 | 5067 | V | 35.2235 |
| 4 | 3.509 | 9172 | 1443 | V | 4.2520 |
| 5 | 3.642 | 1691 | 333 | V | 0.7838 |
| 6 | 3.912 | 10988 | 1054 | V | 5.0938 |
| 7 | 4.184 | 1527 | 210 | V | 0.7079 |
| 8 | 4.346 | 4554 | 560 | V | 2.1114 |
| 9 | 4.734 | 4566 | 384 | V | 2.1166 |
| 10 | 5.096 | 1903 | 223 | V | 0.8824 |
| 11 | 5.558 | 6961 | 330 | V | 3.2269 |
| 12 | 6.145 | 18958 | 529 | V | 8.7888 |
| | | 215705 | 21430 | | 100.0000 |

TABLE 3

For FIG. 3

| No. | Time | Area | Height | MK | Concentration |
|---|---|---|---|---|---|
| 1 | 2.480 | 174804 | 27560 | | 17.8739 |
| 2 | 2.670 | 511089 | 27464 | V | 52.2595 |
| 3 | 3.493 | 58848 | 3382 | V | 6.0173 |
| 4 | 3.728 | 109550 | 3211 | V | 11.2017 |
| 5 | 4.359 | 37656 | 2055 | V | 3.8504 |
| 6 | 4.746 | 30010 | 1472 | V | 3.0685 |
| 7 | 5.107 | 56027 | 1068 | V | 5.7288 |
| | | 977983 | 66212 | | 100.0000 |

Inferences/Conclucion/Summary of Observation

In Vitro Screening of Antitubercular Activity of Plant Extract or its Fractions Against *Mycobacterium Tuberculosis* and Determination of Minimum Inhibitory Concentration The antitubercular activity of a plant extract or its fractions was determined by inhibition of growth and colony forming ability of *M. tuberculosis* H37Rv on 7H10 Middlebrook's medium containing OADC (B-D,USA). The medium was autoclaved and supplemented with OADC and 2 ml was dispensed in sterile tubes. A suspension of 1 mg/ml concentration of plant extract/its fractions was prepared in DMSO (dimethyl sulphoxide), which was added into test tubes containing supplemented medium at different concentrations keeping the volume constant, i.e., 0.1 ml. After proper mixing, the tubes were kept in slanting position and allowed to cool and solidify. These tubes were incubated at 37° C. for 24 hours to observe any contamination. If not, the tubes were streaked with a culture suspension of *M. tuberculosis* H37Rv ($1\text{-}5\times10^4$ bacilli/tube). The inoculated tubes were incubated at 37° C. along with two controls. One, in which no inhibitory compound was present but streaked with the same inoculum of *M. tuberculosis* H37Rv and second, in which a standard antitubercular compound was added at the reported minimum inhibitory concentration (MIC) which will inhibit the growth of tubercle bacilli. Growth of bacilli was observed till 4 weeks of incubation. Extract/fractions containing tubes were compared with control tubes described above. Complete inhibition of growth was recorded as MIC (μg/ml).

In Vitro Antitubercular Activity and MIC of Plant Extract or its Fractions

Two batches of plant extract prepared independently were tested against *M. tuberculosis* H37Rv. Both batches were found effective and completely inhibited the growth of tubercle bacilli at 50 μg/ml present in the medium. At next doubling diluted concentration of the extract (i.e., 25 μg/ml), partial inhibition of growth was observed and at lower concentrations there was no inhibition observed. Hence the MIC of the plant extract was determined to be 50 μg/ml. The plant extract was fractionated into different fractions (F1 to F5) as described above. All the fractions had inhibitory activity against *M. tuberculosis* H37Rv and the MIC was clearly 50 μg/ml.

In Vivo Screening of Antitubercular Activity of Plant Extract or its Fractions Against *Mycobacterium Tuberculosis* in Infected Mice Model of Experimental Tuberculosis

*M. tuberculosis* H37Rv, grown on L-J slants, was harvested and a homogeneous suspension was prepared in Tween-saline at approximately $1\text{-}3\times10^8$ bacilli/ml. Aqueous solutions of sparfloxicin and the plant extract or its fractions were prepared. Female swiss mice, bred in the animal house of Central Drug Research Institute, Lucknow, India and weighing 18-20 g were taken. The mice were divided in four groups with ten mice in each group. Infection of mice with *M. tuberculosis* H37Rv ($1-3\times10^7$ bacilli/mouse) was carried out by injecting 0.1 ml of the bacterial suspension as prepared and described above via lateral tail vein. Treatment of mice with sparfloxicin and plant extract or its fractions was started after 72 hours post infection via intra peritoneal/oral route. The description and treatment of the four groups is as follows:

Group I. Uninfected, untreated mice

Group II. Infected, untreated mice

Group III. Infected but treated with sparfloxicin at 25 mg/kg body weight for 10 days after infection.

Group IV. Infected but treated with plant extract or its fractions at 100 mg/kg body weight for 10 days after infection.

Mice were observed up to 35 days post infection. Mean survival time (MST), percent survival of mice, general health and appearance, body weight, bacillary load in the lungs, enlargement of spleen and lung lesions were observed as parameters to assess the effect of the test plant extract or its fractions as compared to untreated, uninfected or infected or infected but sparfloxicin treated mice.

In Vivo Antitubercular Activity of Plant Extract Against *Mycobacterium Tuberculosis* H37Rv in Infected Mice.

All the mice in group I remained healthy and gained weight during the duration of observation. The mice in Group II began to loose weight after 10 days following infection. They looked weak with ruffled hairs and mortality began after 14 days of infection. All the mice died of tuberculosis within 20-22 days. The spleens were enlarged with visible lesion in the lungs. The average load of bacilli was more than $10^6$/g of lung. All the mice in group III which were treated with sparfloxicin were healthy, gained weight and none of the mice died. The mice treated with plant extract were protected from challenge of *M. tuberculosis* H37Rv as the mean survival time, as compared to untreated infected group, was enhanced. 30-40% of the mice in this group survived the entire period of observation. When these surviving mice were examined, the spleen was not enlarged, there were few lesions in the lung and the load of bacilli was at least 10-fold less in the lung tissue.

As a result of this invention, *Salicornia* which hitherto has been not studied for its bioactivity has become more commercially attractive to cultivate on saline soil for the newly identified application as a source of bioactive extract. The plant possesses bioactivity at mature stage, which allows for better utilization of the plant. The aqueous extract of the plant part has shown the highest activity, which makes the process of preparing extract more natural. The plant material retains activity when stored under ambient conditions and the extract prepared from the plant also retains total activity up to a minimum of 2 years.

Fractions from the active plant extract are prepared by treating the extract successively with solvent mixtures having different polarities, with a view to enhancing the concentration of the active substance. The extracts and fractions are subjected to scientific screening against *M. tuberculosis*, H37Rv, both under in vitro and in vivo conditions. The most effective extract/fraction is identified by screening.

The fractions of the invention or the crude extract can be administered as such to the patient suffering from tuberculosis or can be administered in any conventional dosage form in combination with pharmaceutically acceptable additives such as carriers, dispersants, diluents, flavoring agents and the like. Conventional forms of administration include in the form of a tablet, powder, solution, lozenge, capsules and also injectable forms.

The Main Advantages of the Present Invention are:
1. A preparation of novel anti tubercular herbal extract from marshy, succulent halophytic plant available naturally in wild in the coastal regions of India and elsewhere.
2. The source used in present invention is of edible and of nontraditional nature and grows under seawater inundated conditions in coastal marshy silty clay soil/areas having scope and viability of new sea water agriculture arena.
3. The plant is also a source of good vegetable oil as well of herbal/vegetable salt but not yet used for biological activity anywhere in the world.
4. The specific bioactivity resides in the entire plant and is not restricted to a specific plant part.

We claim:

1. A method for treating tuberculosis in a subject suffering therefrom comprising administering a pharmaceutically effective amount of an antitubercular extract obtained from *Salicornia brachiata* to the subject infected by *Mycobacterium tuberculosis*.

2. The method according to claim 1 wherein the antitubercular extract is obtained from a plant part selected from the group consisting of a whole plant without roots, a root, a spike, a husk, and a seed.

3. The method according to claim 2 wherein the plant part is a root.

4. A method for treating tuberculosis in a subject suffering therefrom comprising administering an antitubercular fraction obtained from an extract of *Salicornia brachiata* a pharmaceutically effective amount of to the subject infected by *Mycobacterium tuberculosis*.

5. The method according to claim 4 wherein the extract is obtained from a plant part selected from the group consisting of a whole plant without roots, a root, a spike, a husk, and a seed.

6. The method according to claim 5 wherein the plant part is a root.

7. The method according to claim 5 wherein the extract is an aqueous extract obtained by extracting the plant part with 100% water.

8. The method according to claim 5 wherein the extract is an alcohol extract obtained by extracting the plant part with methanol or butanol.

9. The method according to claim 4 wherein the antitubercular fraction is obtained by fractionating the extract with methanol:chloroform of 1:1.

10. The method according to claim 5 wherein the antitubercular fraction is obtained by extracting the plant part with methanol:water from 95:5 to 1:1.

11. The method according to claim 4 wherein the antitubercular fraction is obtained by fractionating the extract sequentially with neat butanol, methanol:chloroform (1:1), neat methanol, methanol:water (1:1), or 100% water.

12. The method according to claim 4 wherein the antitubercular fraction is administered in a form selected from the group consisting of tablet, lozenge, capsule, powder, or solution.

13. The method according to claim 4 wherein the antitubercular fraction is administered by a route selected from the group consisting of intravenous and oral.

14. The method according to claim 4 wherein the antitubercular fraction is obtained by fractionation of the extract at ambient temperature.

15. The method according to claim 4 wherein the antitubercular fraction is obtained by fractionation of the extract in solvent mixtures having different polarity.

16. The method according to claim 5 wherein the plant part is washed and dried at a temperature from 20° C. to 35° C. until the moisture content is from 0.5% to 1.5%.

17. The method according to claim 2 wherein the Antitubercular extract is obtained by pulverizing the plant part soaking the plant part in deionized water, and heating the plant part in a water bath at a temperature from 80° C. to 90° C. for a time from 72 hours to 120 hours.

18. The method according to claim 1 wherein the antitubercular extract is concentrated at a temperature from 45° C. to 55° C. or at ambient temperature through an aqueous herbal concentrator.

19. The method according to claim 1 wherein the antitubercular extract is concentrated by freeze drying at a temperature from −50° C. to −60° C. for a time from 8 hours to 16 hours.

20. The method according to claim 2 wherein the plant part is washed and dried at a temperature from 20° C. to 35° C. until the moisture content is from 0.5% to 1.5%.

* * * * *